United States Patent
Spivey

(10) Patent No.: US 8,623,011 B2
(45) Date of Patent: Jan. 7, 2014

(54) MAGNETIC SURGICAL SLED WITH LOCKING ARM

(75) Inventor: James T. Spivey, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1125 days.

(21) Appl. No.: 12/576,514

(22) Filed: Oct. 9, 2009

(65) Prior Publication Data

US 2011/0087223 A1    Apr. 14, 2011

(51) Int. Cl.
*A61B 18/04* (2006.01)

(52) U.S. Cl.
USPC .............................. 606/41; 606/27

(58) Field of Classification Search
USPC ............ 606/27, 34, 41, 51, 205–207
See application file for complete search history.

(56) References Cited

U.S. PATENT DOCUMENTS

| | | | |
|---|---|---|---|
| 3,710,399 A | 1/1973 | Hurst | |
| 4,146,030 A * | 3/1979 | Holroyd | 606/26 |
| 4,278,077 A | 7/1981 | Mizumoto | |
| 4,597,390 A | 7/1986 | Mulhollan et al. | |
| 5,540,648 A | 7/1996 | Yoon | |
| 5,735,842 A | 4/1998 | Krueger et al. | |
| 5,807,235 A | 9/1998 | Heff | |
| 6,315,789 B1 | 11/2001 | Cragg | |
| 6,371,952 B1 | 4/2002 | Madhani et al. | |
| 6,471,172 B1 | 10/2002 | Lemke et al. | |
| 6,776,165 B2 | 8/2004 | Jin | |
| 6,936,003 B2 | 8/2005 | Iddan | |
| 6,986,738 B2 | 1/2006 | Glukhovsky et al. | |
| 7,039,453 B2 | 5/2006 | Mullick et al. | |
| 7,042,184 B2 | 5/2006 | Oleynikov et al. | |
| 7,066,879 B2 | 6/2006 | Fowler et al. | |
| 7,083,579 B2 | 8/2006 | Yokoi et al. | |
| 7,083,617 B2 | 8/2006 | Kortenbach et al. | |
| 7,169,104 B2 | 1/2007 | Ueda et al. | |
| 7,199,545 B2 | 4/2007 | Oleynikov et al. | |
| 7,211,094 B2 | 5/2007 | Gannoe et al. | |
| 7,241,290 B2 | 7/2007 | Doyle et al. | |
| 7,429,259 B2 | 9/2008 | Cadeddu et al. | |
| 8,409,076 B2 | 4/2013 | Pang et al. | |
| 2001/0051766 A1 | 12/2001 | Gazdzinski | |
| 2003/0060702 A1 | 3/2003 | Kuth et al. | |
| 2003/0114731 A1 | 6/2003 | Cadeddu et al. | |
| 2004/0064153 A1 | 4/2004 | Creighton, IV et al. | |
| 2004/0093039 A1 | 5/2004 | Schumert | |
| 2005/0085697 A1 | 4/2005 | Yokoi et al. | |

(Continued)

OTHER PUBLICATIONS

PCT International Search Report and Written Opinion issued in International application No. PCT/US2010/051990, dated Jul. 13, 2011.

(Continued)

*Primary Examiner* — Michael Peffley
*Assistant Examiner* — Daniel Fowler

(57) ABSTRACT

A surgical device comprises an ex vivo magnet and an in vivo sled magnetically attracted to the ex vivo magnet. The sled can be positioned and anchored within a patient by moving the ex vivo magnet. The sled defines a longitudinal axis. An arm extends from the sled. The arm being moveable relative the sled between a retracted position and an extended position. The arm comprises an end effector. A locking mechanism operatively connected to the arm to lock the arm in the retracted and extended positions. The mechanism may include a rack that both rotates about a pinion and translates tangentially about the pinion.

11 Claims, 5 Drawing Sheets

(56) References Cited

U.S. PATENT DOCUMENTS

| | | |
|---|---|---|
| 2005/0119640 A1 | 6/2005 | Sverduk et al. |
| 2005/0272972 A1 | 12/2005 | Iddan |
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0084885 A1 | 4/2006 | Reydel |
| 2006/0149135 A1 | 7/2006 | Paz |
| 2006/0195015 A1 | 8/2006 | Mullick et al. |
| 2006/0229592 A1 | 10/2006 | Yokoi et al. |
| 2007/0010709 A1 | 1/2007 | Reinschke |
| 2007/0032700 A1 | 2/2007 | Fowler et al. |
| 2007/0032701 A1 | 2/2007 | Fowler et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2008/0004634 A1 | 1/2008 | Farritor et al. |
| 2008/0015413 A1 | 1/2008 | Barlow et al. |
| 2008/0015552 A1 | 1/2008 | Doyle et al. |
| 2008/0058835 A1 | 3/2008 | Farritor et al. |
| 2008/0221591 A1 | 9/2008 | Farritor et al. |
| 2008/0269779 A1 | 10/2008 | Cadeddu et al. |
| 2009/0005636 A1 | 1/2009 | Pang et al. .................... 600/102 |
| 2009/0012530 A1 | 1/2009 | Fowler |
| 2009/0043246 A1 | 2/2009 | Dominguez |
| 2009/0048612 A1 | 2/2009 | Farritor et al. |
| 2009/0054909 A1 | 2/2009 | Farritor et al. |
| 2009/0171373 A1 | 7/2009 | Farritor et al. |

OTHER PUBLICATIONS

International Search Report for International Application No. PCT/US2010/051990, dated Jul. 13, 2011.

\* cited by examiner

US 8,623,011 B2

MAGNETIC SURGICAL SLED WITH LOCKING ARM

BACKGROUND

The present invention relates in general to surgical devices and procedures, and more particularly to minimally invasive surgery.

Surgical procedures are often used to treat and cure a wide range of diseases, conditions, and injuries. Surgery often requires access to internal tissue through open surgical procedures or minimally invasive surgical procedures. Minimally invasive surgery often involves using an endoscope, such as laparoscopes, arthroscopes, and flexible endoscopes, to visualize internal tissue of a patient, which sometimes referred to as "endoscopic surgery". Endoscopes and instruments are typically introduced into a patient through percuateous punctures or incisions, or through a patient's natural orifices to access intraluminal anatomy or for transluminal procedures.

Minimally invasive surgery has numerous advantages compared to traditional open surgical procedures, including reduced trauma, faster recovery, reduced risk of infection, and reduced scarring. Minimally invasive surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars may be used to provide a port through which endoscopes and surgical instruments are passed. Trocars generally have an instrument seal, which prevents the insufflatory fluid from escaping while an endoscope or surgical instrument is positioned in the trocar.

While a wide range of minimally invasive surgical devices and techniques have been used, one has previously made or used the devices and techniques in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, like-numbered references refer to the same elements in the various figures. Unless otherwise indicated, the figures are not necessarily drawn to scale, but rather to illustrate the principles of the invention.

DETAILED DESCRIPTION

Figure 1:
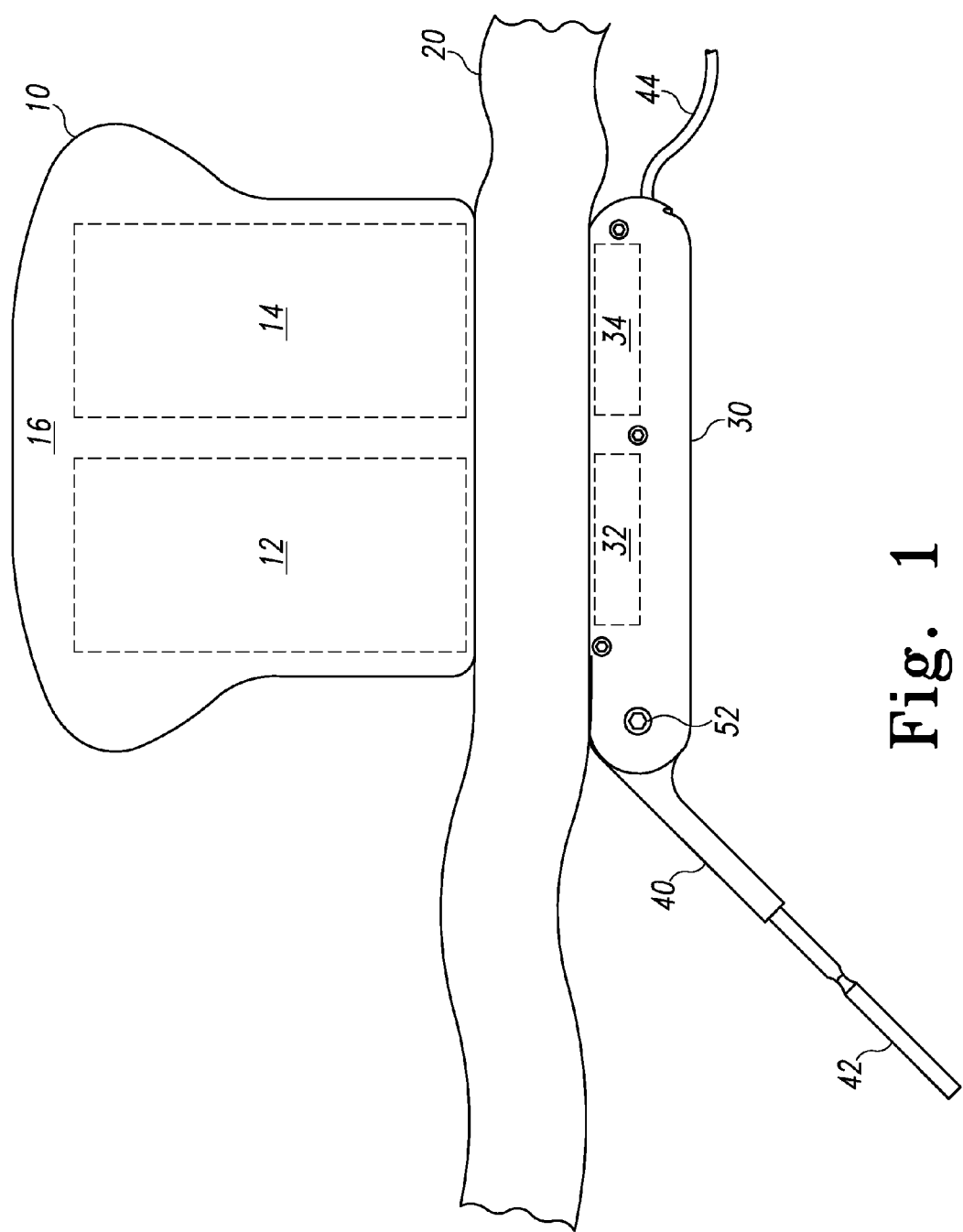
FIG. 1 depicts a side view of a magnetically anchored surgical sled with an arm in an extended position.

The embodiment shown in FIG. 1 comprises an anchor (10) and a sled base (30). Patient tissue (20), such as the abdominal wall, an organ wall, or the like, is interposed between the anchor (10) and the sled base (30). The anchor (10) and sled base (30) and magnetically coupled to each other through the tissue (20). By sliding the anchor (10) relative the tissue (2), the surgeon can position the sled base (30) in a desired location. Likewise, by keeping the anchor (10) stationary relative the tissue (20), the surgeon can anchor the sled base (30) in a desired location. The anchor (10) will often be positioned ex vivo and the sled base (30) positioned in vivo.

In the present embodiment, the anchor (10) includes two magnets (12, 14). The magnets (12, 14) are contained within a casing (16) that forms an ergonomic handle. The magnets (12, 14) can take a variety of forms such as permanent magnets, rare earth magnets, electromagnets, and the like. The magnets (12, 14) are magnetically coupled to supports (32, 34). The present embodiment the supports (32, 34) may be formed from a magnetic materials, such as any of a variety of known ferromagnetic materials or magnets. The pairing of two magnets (12, 14) with supports (32, 34), respectively, facilitate in vivo angular orientation of the sled base (30). For instance, by rotating the anchor (10) relative the tissue (20), the sled base (30) will likewise rotate.

The sled base (30) can take a variety of different shapes and sizes; however, in the present embodiment the sled base (30) is generally cylindrical in shape and sized to pass through a standard trocar, such as a 12 mm, 18 mm, or 20 mm trocar. The nominal length of the sled base (30) may be between 60-90 mm, more preferably between 65-80 mm, and most preferably between 70-75 mm. The nominal diameter is the sled base (30) may be between 12-19 mm, more preferably between 13-17 mm, and most preferably between 14-16 mm. The arm may be between 40 and 80 mm in length.

An arm (10) is connected to the sled base (30). The arm (40) in the present example is substantially straight and rigid; however, curved, articulating, steerable arms, or flexible are also contemplated. The arm (40) includes an end effector (42), which in this example is a mono-polar electro-cautery tip. A variety of other end effectors could also be used, including graspers, scissors, ultrasonic blades, bi-polar clamps, surgical staplers, ultrasonic sensors, cameras, suturing devices, and the like. A tether (44) is operatively connected to the end effector (42) and extends from the sled base (30). In the present example the tether (44) is a wire to deliver electrical energy to the electro-cautery tip; however, the type of tether (44) may depend upon the end effector (42). For instance, the tether could include push/pull wires to deliver forces, tubes to deliver fluids or pressure, fiber optic cables to deliver light or signals, electrical wires to deliver electricity or signals, and the like.

Figure 2:
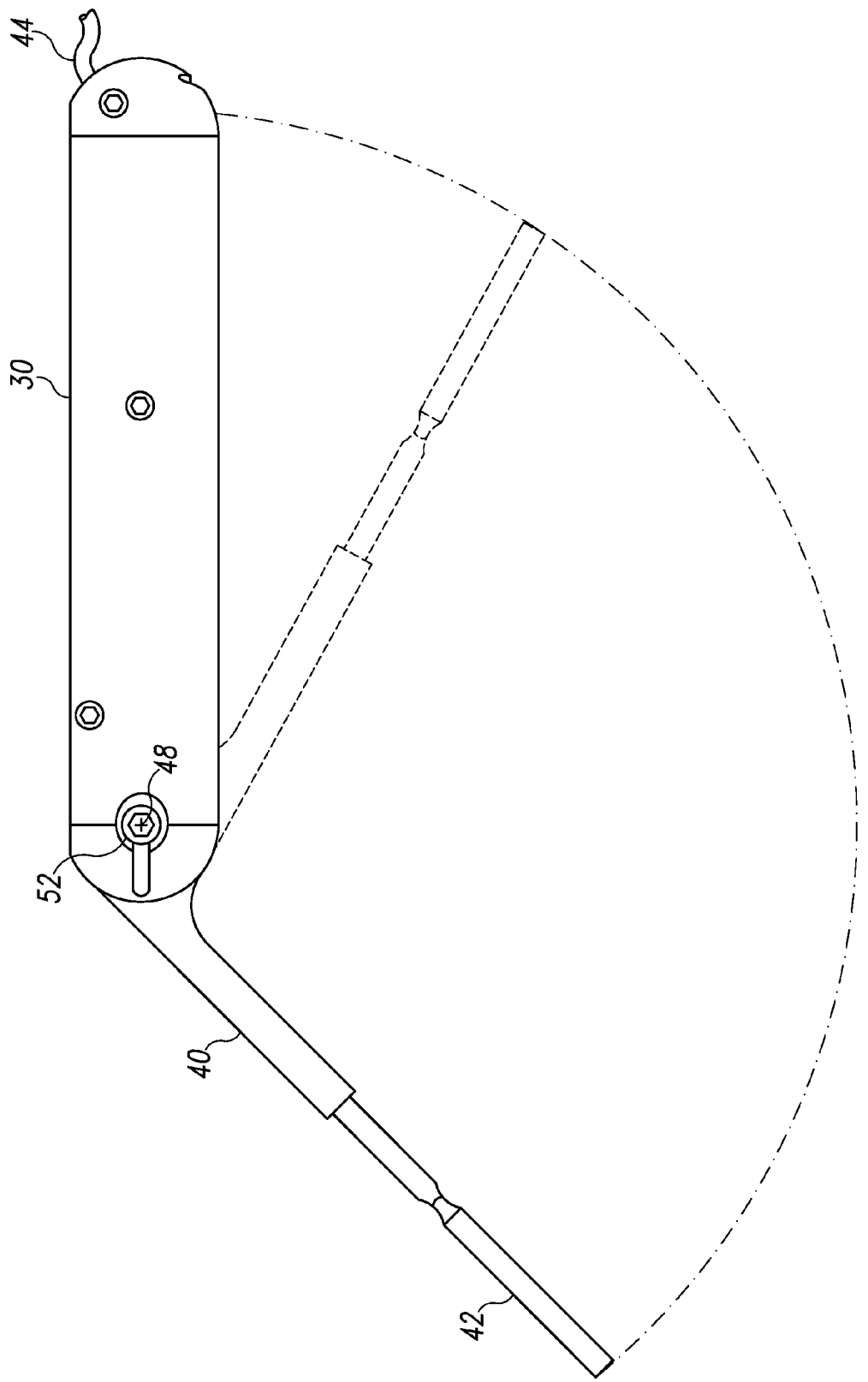
FIG. 2 depicts a cross-sectional view of a surgical sled with an pivoting arm.
Figure 3:
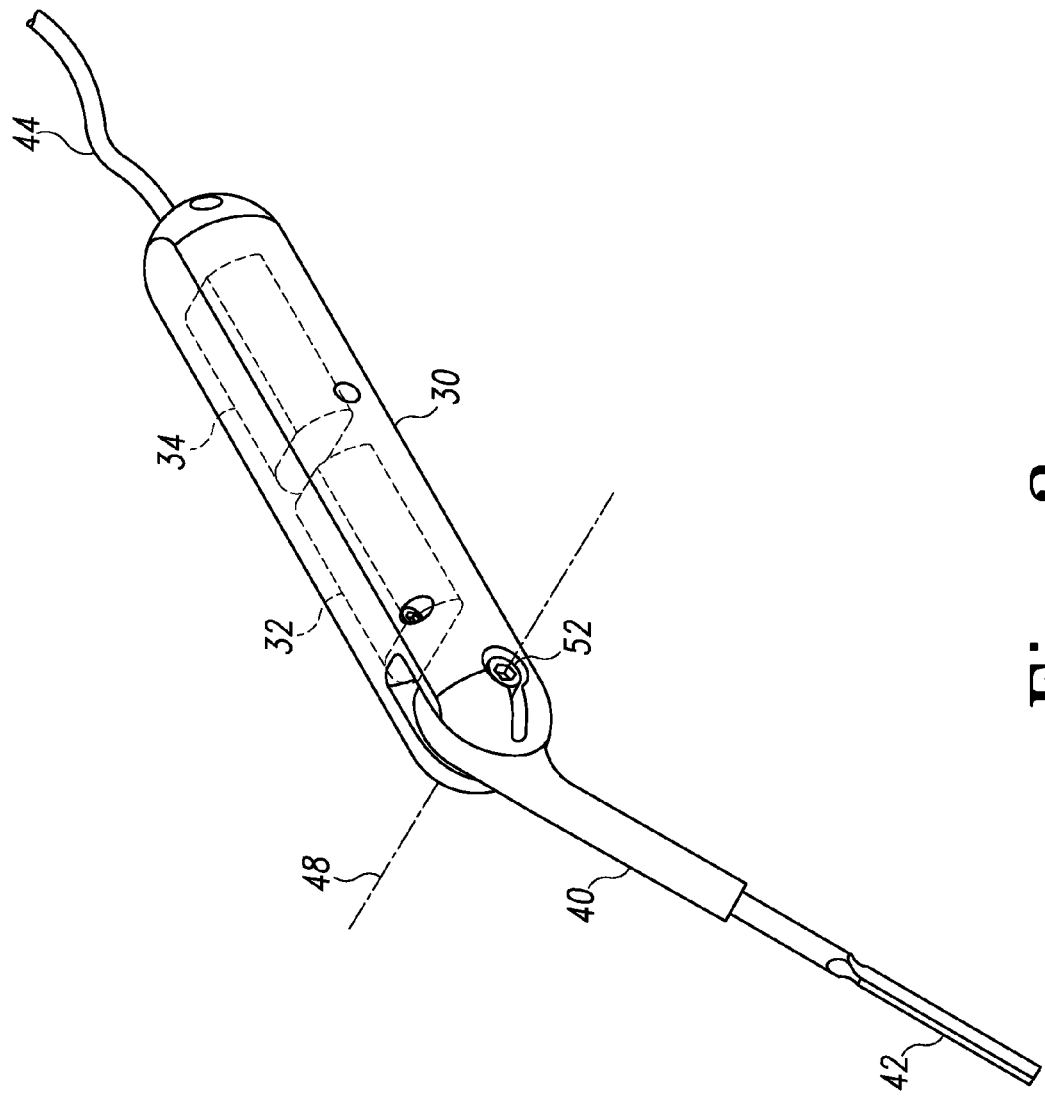
FIG. 3 depicts a isometric view of a surgical sled with an arm in an extended retracted position.

As shown in FIG. 2, the arm (40) pivots relative the sled base (30) about the pivot axis (48) between a refracted position and an extended position. Preferably the arm (40) is at least partially recessed within the sled base (30) when the arm (40) is in the retracted position.

As shown in FIGS. 4-8, the device includes a mechanism operative to both actuate the arm (40) between the retracted and extended positions and lock the arm (40) in the retracted and extended positions. A pinion (50) rotates about the axis (48) independently of both the sled body (30) and the arm (40). The pinion (50) is captured within the ring (49) allowing relative rotation between the two components. The ring (49) is connected to the arm (40). Connected to the pinion (50) is a head (52) accessible from one or both external sides of the sled base (30). Any of a variety of head configurations may be used, including a hex ball head, hex head, flat head, phillips head, and the like.

The ring (49) includes a track (46) that is tangential to the pinion (50). As the arm (40) pivots about the axis (48), the ring (49) and track (46) rotate about the axis (48). A floating rack (54) is received by the track (46) such that rack (54) is translatable along the track (46). The rack (54) engages the pinion (50). In operation the rack (54) both rotates about the pinion (50) and translates tangentially about pinion (54).

The sled base (30) includes a first relief (36) and a second relief (38) each dimensioned to receive the rack (54). The first and second reliefs (36, 38) are angularly offset from each other about the axis (48). The first relief (36) is aligned with the track (46) when the arm (40) is in the extended position, and the second relief (38) is aligned with the track (46) when the arm (40) is in the retracted position. The sled base (30) comprises an arcuate wall (39) about the axis (48) extending between the first and second reliefs (36, 38). The ring (49) is captured within the arcuate wall (39) allowing relative rotation between the two components.

Figure 4:
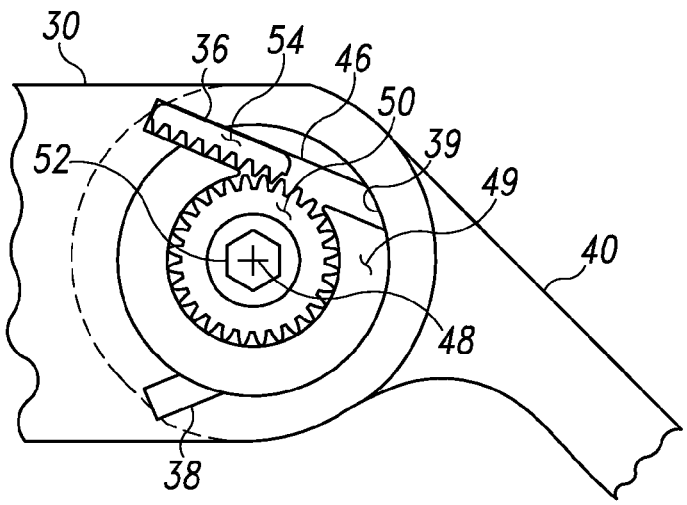
FIG. 4 depicts a cross sectional view of a locking and actuating mechanism locked with the arm in the extended position.

FIGS. 4-8 sequentially illustrate the locking and actuating mechanism in operation. As shown in FIG. 4, the rack (54) is positioned in both the first relieve (36) and in the track (46). In this orientation, the rack (54) prevents relative rotation between the ring (49) and sled body (30) thus locking the arm (40) in the extended position.

Figure 5:
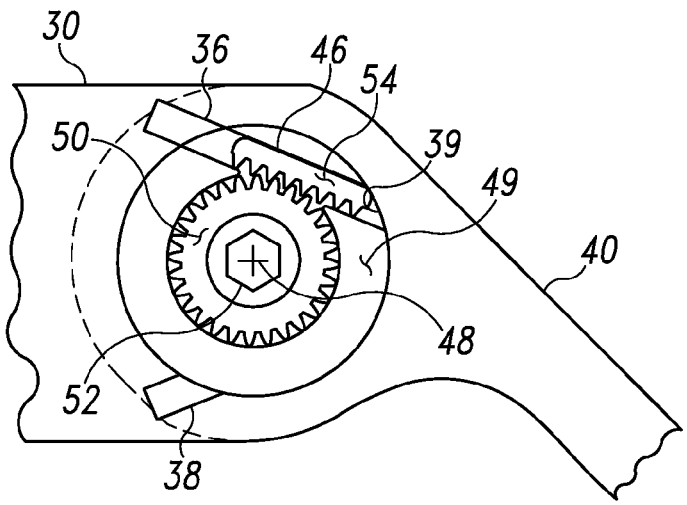
FIG. 5 depicts a cross sectional view of a locking and actuating mechanism unlocked with the arm in the extended position.

To unlock the arm (40), the surgeon will place a torque tool into the head (52) and rotate the tool clockwise, thus imparting a clockwise torque on the pinion (50). As shown in FIG. 5, the rotating pinion (50) will translate the rack (54) out of the first relief (36) and along the track (46) until it contacts the arcuate wall (39). In this configuration the arm (40) is unlocked.

Figure 6:
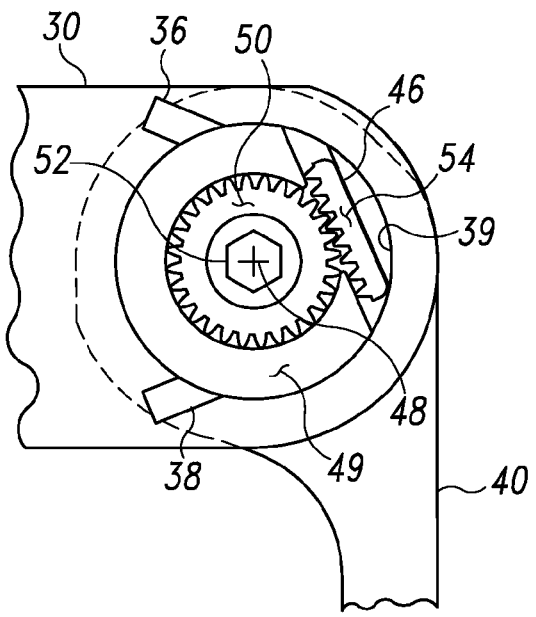
FIG. 6 depicts a cross sectional view of a locking and actuating mechanism unlocked with the arm pivoting from the extended position to the retracted position.

As shown in FIG. 6, continued clockwise rotation of the tool and pinion (50) will impart a clockwise torque on the ring (49) because the arcuate wall (39) prevents further translation of the rack (54) within the track (46). The imparted torque on the ring (49) causes the arm (40) to rotate clockwise. Note that as the arm (40) rotates, the track (46) is no longer in alignment with the first relief (36).

Figure 7:
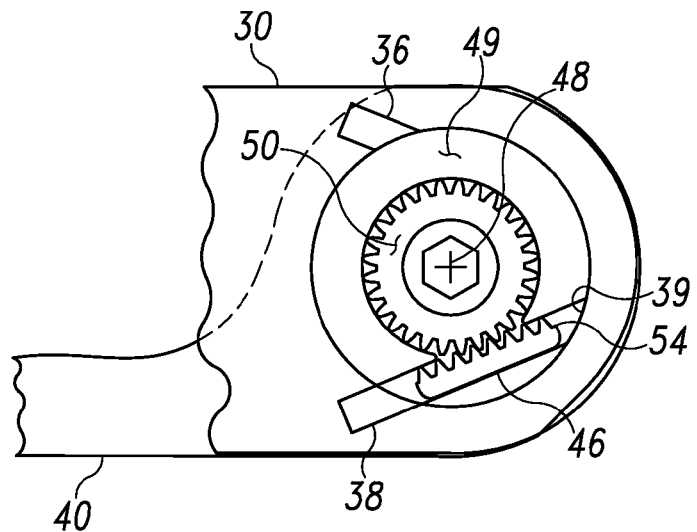
FIG. 7 depicts a cross sectional view of a locking and actuating mechanism unlocked with the arm in the retracted position.
Figure 8:
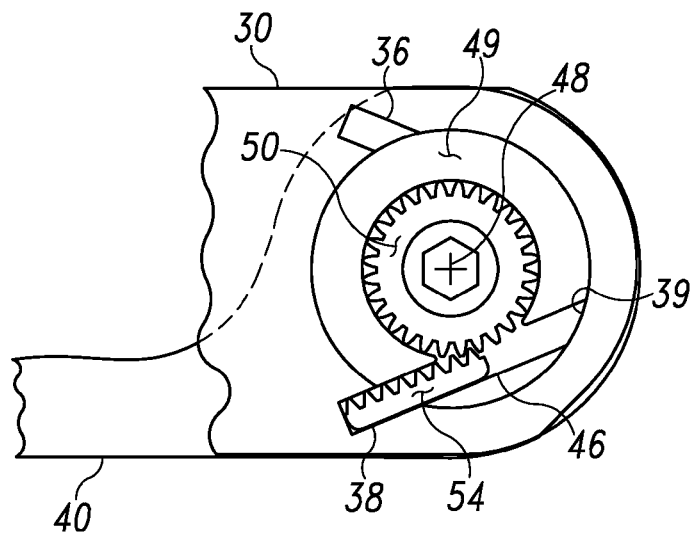
FIG. 8 depicts a cross sectional view of a locking and actuating mechanism locked with the arm in the retracted position.

As shown in FIG. 7, continued clockwise rotation of the tool and pinion (50) will continue to rotate the arm (40) until the track (46) aligns with the second relief (38). In this configuration the arm (40) is in its retracted position and unlocked. Because the second relief (38) is aligned with the track (46), the arcuate wall (39) no longer prevents the rack (54) from translating in the track (46). Accordingly, continued clockwise rotation of the tool and pinion (50) will translate the rack (54) into the second relief (38) as shown in FIG. 8. The rack (54) is positioned in both the second relieve (38) and in the track (46), thus preventing relative rotation between the ring (49) and sled body (30) and locking the arm (40) in the retracted position.

As one with ordinary skill in the art will recognize, unlocking and extending the arm (40) can be achieved by turning the tool counterclockwise, thus reversing the foregoing sequence.

The following is one example of the device being used. The sled base (30) is delivered into a patient's peritoneal cavity, preferably when the cavity is insufflated, with the arm (40) in the retracted position. The delivery may be through a percutaneous incision, such as through a trocar or other access device, or through a NOTES incision, such as transgastric, transvaginal, transcolonic, and the like. If the sled base (30) includes a tether (44), it may be passed through the delivery incision or through a separate incision. The anchor (10) is placed ex vivo on the abdomen to attract and anchor the sled base (30) to the abdominal wall. A slender rotational driver is passed into the peritoneal cavity through the same incision or a separate trocar. The rotational driver is dimensioned to mate with the head (52) and may be rigid or flexible. Usually under visualization from an endoscope, the driver is then positioned into the head (52) and rotated, either manually or with a motor, to pivot the arm (40) to the extended position. The driver may then be removed from the surgical field. The surgeon will typically move and rotate the anchor (10) across the abdomen, and the sled base (30) will follow due to the magnet attractions. By palpating and deflecting the abdomen with the anchor (10), either straight down or at an angle, the surgeon can move the end effector (42) to a desired location in the peritoneal cavity to perform a surgeon procedure. After completing the procedure, the driver may be reintroduced to the peritoneal cavity, into the head (52), and rotated in the opposite direction to pivot the arm (40) to its retracted. The anchor (10) may then be removed from the abdomen, thus releasing the sled base (30) from the abdominal wall. The sled base (30) and driver may then be removed from the surgical field.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical device, comprising:
   a) an ex vivo magnet;
   b) an in vivo sled magnetically attracted to the ex vivo magnet, whereby the sled can be positioned and anchored within a patient by moving the ex vivo magnet, the sled defining a longitudinal axis;
   c) an arm extending from the in vivo sled, the arm being moveable relative to the sled between a retracted position and an extended position, the arm comprising a surgical end effector:
   d) a rack and pinion operatively connected to the arm to lock the arm in the retracted and extended positions; and
   e) a track tangential to the pinion, the track receiving the rack, the track connected to the arm and rotatable about the arm pivot axis as the arm pivots.

2. A surgical device, comprising:
   a) an ex vivo magnet;

b) an in vivo sled magnetically attracted to the ex vivo magnet, whereby the sled can be positioned and anchored within a patient by moving the ex vivo magnet, the sled defining a longitudinal axis;

c) an arm extending from the in vivo sled, the arm being moveable relative to the sled between a retracted position and an extended position, the arm comprising a surgical end effector;

d) a rack and pinion operatively connected to the arm to lock the arm in the retracted and extended positions; and e) a first relief in the sled dimensioned to receive the rack and a second relief in the sled dimensioned to receive the rack, the second relief angularly offset about the arm pivot axis from the first relief.

3. A surgical device, comprising:

a) an ex vivo magnet;

b) an in vivo sled magnetically attracted to the ex vivo magnet, whereby the sled can be positioned and anchored within a patient by moving the ex vivo magnet, the sled defining a longitudinal axis;

c) an arm extending from the in vivo sled, the arm being moveable relative to the sled between a retracted position and an extended position, the arm comprising a surgical end effector; and d) a rack and pinion operatively connected to the arm to lock the arm in the retracted and extended positions, wherein the rack both rotates about the pinion and translates tangentially about the pinion.

4. The surgical device of claim 3, wherein the end effector is an electro-cautery tip.

5. The surgical device of claim 3, further comprising a tether operatively connected to the end effector and extending from the sled.

6. A surgical device, comprising:

a) an anchor;

b) a sled magnetically attracted to the anchor whereby the sled can be positioned within a patient by moving the anchor;

c) an arm extending from the sled, the arm being moveable relative to the sled between a retracted position and an extended position, the arm comprising a surgical end effector; and d) a rack and pinion operative to both actuate the arm between the retracted and extended positions and lock the arm in the retracted and extended positions, wherein the rack both rotates about the pinion and translates tangentially about the pinion.

7. A surgical device, comprising:

a) an arm extending from a base, the arm pivoting relative to the base about an axis between a first position and an second position, the arm comprising a surgical end effector;

b) a pinion rotatable about the arm pivot axis;

c) a track tangential to the pinion, the track connected to the arm and rotatable about the arm pivot axis as the arm pivots;

d) a rack engaging the pinion and translatable along the track;

e) a first relief in the base dimensioned to receive the rack, the first relief being aligned with the track when the arm is in the first position; and f) a second relief in the base dimensioned to receive the rack, the second relief being aligned with the track when the arm is in the second position.

8. The surgical device of claim 7, wherein the base further comprises an arcuate wall about the arm pivot axis extending between the first and second reliefs.

9. The surgical device of claim 7, further comprising an ex vivo magnet, wherein the base is magnetically attracted to the ex vivo magnet and can be positioned within a patient by moving the ex vivo magnet.

10. The surgical device of claim 7, wherein the pinion rotates independently of the body and the arm.

11. The surgical device of claim 7, wherein the second relief angularly offset from the first relief about the arm pivot axis.

\* \* \* \* \*